United States Patent
Schöller et al.

(10) Patent No.: US 7,305,987 B2
(45) Date of Patent: Dec. 11, 2007

(54) PROCEDURE FOR THE CONTROL OF A RESPIRATOR DEVICE AS WELL AS APPARATUS FOR MONITORING

(75) Inventors: Bernd Schöller, Karlsruhe (DE); Bernd Graetz, Schenefeld (DE); Jörg Maurer, Aumühle (DE)

(73) Assignee: Gottlieb Weinmann Gerate fur Medizin und Arbeitsschutz GmbH & Co., Hamburg (DE)

( * ) Notice: Subject to any disclaimer, the term of this patent is extended or adjusted under 35 U.S.C. 154(b) by 91 days.

(21) Appl. No.: 09/816,014

(22) Filed: Mar. 23, 2001

(65) Prior Publication Data
US 2001/0039950 A1  Nov. 15, 2001

(30) Foreign Application Priority Data
Mar. 24, 2000  (DE)  ................ 100 14 427

(51) Int. Cl.
*A61M 16/00*  (2006.01)
(52) U.S. Cl. ................. 128/204.18; 128/204.23
(58) Field of Classification Search ........... 128/204.18, 128/204.22, 204.25, 204.26, 205.29, 205.25, 128/204.21, 204.23, 202.22
See application file for complete search history.

(56) References Cited

U.S. PATENT DOCUMENTS

| | | | | |
|---|---|---|---|---|
| 4,414,982 A | * | 11/1983 | Durkan | 128/202.22 |
| 5,107,830 A | * | 4/1992 | Younes | 128/204.18 |
| 5,245,995 A | | 9/1993 | Sullivan et al. | |
| 5,259,373 A | * | 11/1993 | Gruenke et al. | 128/204.23 |
| 5,303,146 A | * | 4/1994 | Ammirato et al. | 715/503 |
| 5,313,937 A | * | 5/1994 | Zdrojkowski | 128/202.22 |
| 5,318,038 A | | 6/1994 | Jackson et al. | |
| 5,540,219 A | * | 7/1996 | Mechlenburg et al. | 128/204.18 |
| 5,558,086 A | * | 9/1996 | Smith et al. | 128/204.23 |
| 5,617,846 A | * | 4/1997 | Graetz et al. | 128/204.21 |
| 5,803,066 A | | 9/1998 | Rapoport et al. | |

(Continued)

FOREIGN PATENT DOCUMENTS

DE  38 20 043 C2  6/1989

(Continued)

OTHER PUBLICATIONS

European Office Action dated Aug. 18, 2003.

(Continued)

*Primary Examiner*—Steven O. Douglas
(74) *Attorney, Agent, or Firm*—Harness, Dickey & Pierce, P.L.C.

(57) ABSTRACT

The procedure and the apparatus serve for the control of a respirator device which is used for the supply of breathable gas to a patient. At least one sensor for the capture of the time-wise evolution of at least one respirator-treatment parameter is provided. The sensor can be arranged in the area of an air delivery which encompasses a respirator device as well as a connecting installation. The sensor is connected to an analyzer which carries out a pattern recognition and which is connected to a control for the modification of at least one respirator-treatment parameter. In order to implement the pattern recognition, one captures—at least at intervals—the time-wise evolution of at least one of the respirator-treatment parameters.

15 Claims, 3 Drawing Sheets

U.S. PATENT DOCUMENTS

| | | | | |
|---|---|---|---|---|
| 5,881,724 A | * | 3/1999 | Graetz et al. | 128/204.21 |
| 5,937,853 A | * | 8/1999 | Strom | 128/204.18 |
| 5,937,854 A | * | 8/1999 | Stenzler | 128/204.18 |
| 6,085,747 A | * | 7/2000 | Axe et al. | 128/204.18 |
| 6,105,575 A | * | 8/2000 | Estes et al. | 128/204.21 |
| 6,142,952 A | * | 11/2000 | Behbehani et al. | 600/533 |
| 6,220,244 B1 | * | 4/2001 | McLaughlin | 128/204.18 |
| 6,257,234 B1 | * | 7/2001 | Sun | 128/204.18 |
| 6,360,740 B1 | * | 3/2002 | Ward et al. | 128/200.24 |
| 6,360,741 B2 | * | 3/2002 | Truschel | 128/202.22 |
| 6,367,474 B1 | * | 4/2002 | Berthon-Jones et al. | 128/204.18 |
| 6,435,182 B1 | * | 8/2002 | Lutchen et al. | 128/200.24 |
| 6,588,422 B1 | * | 7/2003 | Berthon-Jones et al. | 128/204.23 |
| 6,854,462 B2 | * | 2/2005 | Berthon-Jones et al. | 128/204.23 |
| 6,915,803 B2 | * | 7/2005 | Berthon-Jones et al. | 128/204.23 |

FOREIGN PATENT DOCUMENTS

| | | |
|---|---|---|
| DE | 40 38 871 A1 | 6/1992 |
| DE | 37 89 221 T2 | 8/1994 |
| DE | 690 15 818 T2 | 5/1995 |
| DE | 197 17 106 A1 | 10/1998 |
| DE | 198 49 571 A1 | 5/2000 |
| DE | 692 30 637 T2 | 6/2000 |
| DE | 692 30 564 T2 | 8/2000 |
| EP | 0 373 585 A1 | 6/1990 |
| EP | 0 705 615 A1 | 4/1996 |

OTHER PUBLICATIONS

European Search Report dated Feb. 28, 2003.

* cited by examiner

PROCEDURE FOR THE CONTROL OF A RESPIRATOR DEVICE AS WELL AS APPARATUS FOR MONITORING

BACKGROUND AND SUMMARY OF THE INVENTION

The invention concerns a procedure for the control of a respirator device, in which one can set at least two different pressure levels of a breathable-gas supply and in which at least one respirator-treatment parameter is captured by a measurement technique and is evaluated for the purpose of controlling the respirator-treatment pressure.

In addition to the above, the Invention concerns an apparatus for monitoring at least one respirator-treatment parameter when a patient is supplied with the breathable gas. The apparatus features a sensor for capturing the time-wise evolution of the respirator-treatment parameter, the sensor being arranged in an air-delivery area which encompasses a respirator device as well as a connecting installation.

A not inconsiderable number of people suffer from sleep disturbances which affect the daytime well-being of these individuals and which [disturbances] may impair their social and professional capacity as well as quality of their life, to an occasionally considerable extent. One of these sleep disturbances is sleep apnea which is treated primarily with the so-called CPAP therapy (CPAP=Continuous Positive Airway Pressure). In this therapy an airstream consisting of a breathable gas is continuously supplied to the sleeping patient via a nose mask. By means of a hose the mask is connected to a respirator device which encompasses an aerator that produces a gas stream with a gauge pressure of 5 to 20 mbar.

The gas stream is supplied to the patient either under constant pressure or else—in order to facilitate the breathing work—at a lower pressure during the expiration stage. Even though sleep apneas occur only for short periods and make up a minor portion of sleep, in both cases the aerator operates during the entire sleep period (night), a fact which detracts from the acceptability of this sleep apnea treatment.

U.S. Pat. No. 5,245,995 teaches a CPAP respirator device which can be used on patients with sleep apnea. The breathable gas is supplied to the patient via a breathing mask, a source of compressed gas being provided in the area of the device. The source of compressed gas can be controlled as a function of airway resistance.

European Patent No. 0,373,585 describes a method for capturing the breathing resistance of a patient by means of ORM measurements. Here, the volumetric breathing stream is overlaid at a predetermined frequency with an oscillating volumetric stream featuring a low volumetric rise. Because of the periodic pressure variation occurring at the same frequency, one can generate a reading which is a function of the actual airway resistance.

From U.S. Pat. No. 5,318,038 one knows a respiratory measurement which involves the use of a pneumotachygraph in the gas delivery line. European Patent No. 0,705,615 describes a high-quality implementation of control for a respirator device based on the application of ORM measurements.

The procedures and apparatus in the prior art already provide greatly reliable means for preventing the occurrence of conditions threatening the patient's life. However so far it has not been possible to eliminate all impairments of the patient's quality of life. A special goal is to leave intact as much as possible the patient's own breathing activity, providing equipment-based support solely when the latter is indeed needed. This objective requires the optimization of the respirator device's control and regulation, as well as the use of appropriate regulating-technology components. In particular one must recognize at the earliest possible moment the occurrence of deviations from the patient's normal breathing activity, and react to them by means of the appropriate control and regulation of the respirator device.

Consequently it is the task of the present Invention to improve a procedure of the type described at the outset, in a manner such as to promote a prompt adjustment of the device's operation to the respective breathing condition.

This task is achieved by means of the Invention in that at least one respirator-treatment parameter is modified as a function of a pattern recognition. To carry out this pattern recognition, one captures—at least at intervals—the time-wise evolution of at least one respirator-treatment parameter and one analyzes it with respect to a typical individual pattern and/or with respect to an evolution pattern.

It is a further task of the present Invention to design an apparatus of the type described at the outset, in a manner such that, using a simple device structure, early changes in the respective respirator-treatment situation are recognized.

This task is achieved by the Invention in a manner such that the sensor is connected with an analyzer which carries out a pattern recognition, the analyzer being connected to a control installation for modifying at least one respirator-treatment parameter.

Carrying out a pattern recognition makes it possible to detect early changes in an existing breathing condition and thus permits a timely modification in the respirator device's controls. Here, advantage is taken of the fact that a plurality of respirator-treatment conditions are characterized by typical evolution patterns—for instance, of the respirator-treatment pressure or the respirator-treatment flow, or of variables proportional to them. In addition there is also the factor of the relatively early appearance, in the transition from one respirator-treatment condition to another, of typical evolution patterns.

The use of pattern recognition and the prompt introduction of modifications in the device's controls make it possible—even before a change in the respirator-treatment condition, noticeable by the patient, actually occurs—to counteract this change by adjusting the device's controls. The result is that, on one hand, no respirator-treatment conditions negatively affecting the patient's health are reached. On the other hand, the countermeasures are initiated at such an early point that relatively small changes in respirator-treatment parameters suffice to return to the desired normal condition. At the very least, the deviations from such normal conditions are kept within a narrow interval. The early triggering of the measures makes it possible to keep the intensity of those counteracting steps at a very low level which, as a rule, cannot even be noticed by the patient.

For greater ease of detection of significant patterns, it is proposed that the prevailing pressure level for breathing support be temporarily overlaid with a stimulating stream which oscillates at a specific frequency. In particular, this also comprises a change in the respective frequency during the application of the therapy.

A factor which contributes to the patient perception of the device's control setting as being pleasant is that—after the selective evaluation of an oscillatory pressure amplitude at the frequency of the stimulating stream, in the air supply to the patient (corresponding to a specific breathing resistance of the patient)—one carries out a selection of the respective pressure amplitude.

A typical application consists in the implementation of a CPAP respirator treatment.

A class of signals capable of evaluation is defined by the fact that at least one electric signal is evaluated during the pattern recognition.

Consideration is also given to evaluating a physical signal during the pattern recognition. The physical signal can be transformed into an electrical signal for further processing.

In order to support a systematic evaluation of the pattern recognition, it is proposed that in the context of the pattern recognition one carry out a derivation of error classes.

A typical signal evolution to be evaluated is defined in that an OPS signal is evaluated. By OPS signal we refer to an Oscillating Pressure Signal which corresponds to the numerical value of the impedance.

It is also possible that a pressure signal and/or a sound pressure and/or a pressure variation will be evaluated.

Because of the retro-acting effect, exerted by the production of a respirator treatment situation upon the electrical drive conditions of the compressed-air supply, consideration has also been given to evaluating an electrical drive parameter of the compressed-gas supply. This proves particularly practical if the regulation is carried out via an electric drive. Alternatively, however, the regulation can also be carried out independently of the pressure-building drive—e.g., via a valve.

In accordance with a typical evaluation run it is envisaged that, in the pattern recognition, it is distinctive form features that will be evaluated.

Consideration is also given to the possibility that, in the pattern recognition, distinctive time features and/or distinctive amplitude features will be evaluated.

The activation of predefined control runs, as a function of a pattern-recognition result, is promoted by the fact that an assignment to a class is carried out subsequent to the pattern recognition.

In order to increase the evaluation speed it is provided that the analyzer be coupled with a storage for supplying the comparative patterns.

Another contributory factor to a high processing speed is that the analyzer is coupled with a classifier.

A prompt evaluation of the time-wise evolution characteristics of the pattern that is to be evaluated is facilitated by the fact that the analyzer features a time-wise evolution analyzer and/or an amplitude-wise evolution analyzer.

A prompt evaluation of the form-wise evolution characteristics of the pattern that is to be evaluated is facilitated by the fact that the analyzer features a form-wise evolution analyzer.

BRIEF DESCRIPTION OF THE DRAWINGS

Examples of embodiment of the invention are schematically shown in the drawings.

DESCRIPTION OF THE PREFERRED EMBODIMENT

Figure 1:
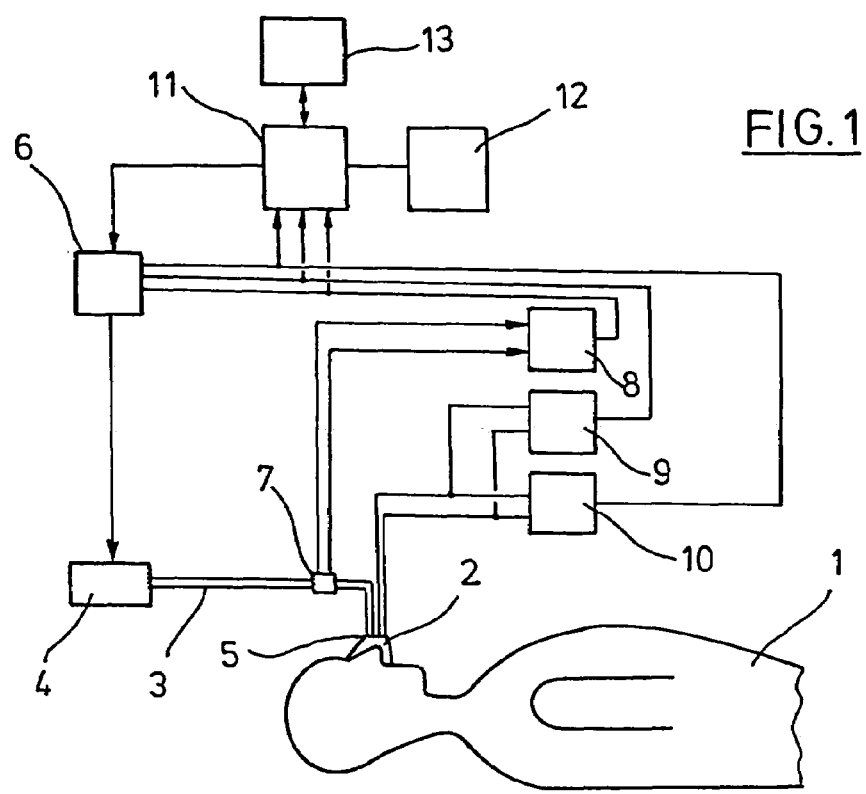
FIG. 1 shows a theoretical block diagram for implementing a CPAP respirator treatment with supplementary pattern recognition.
Figure 2:
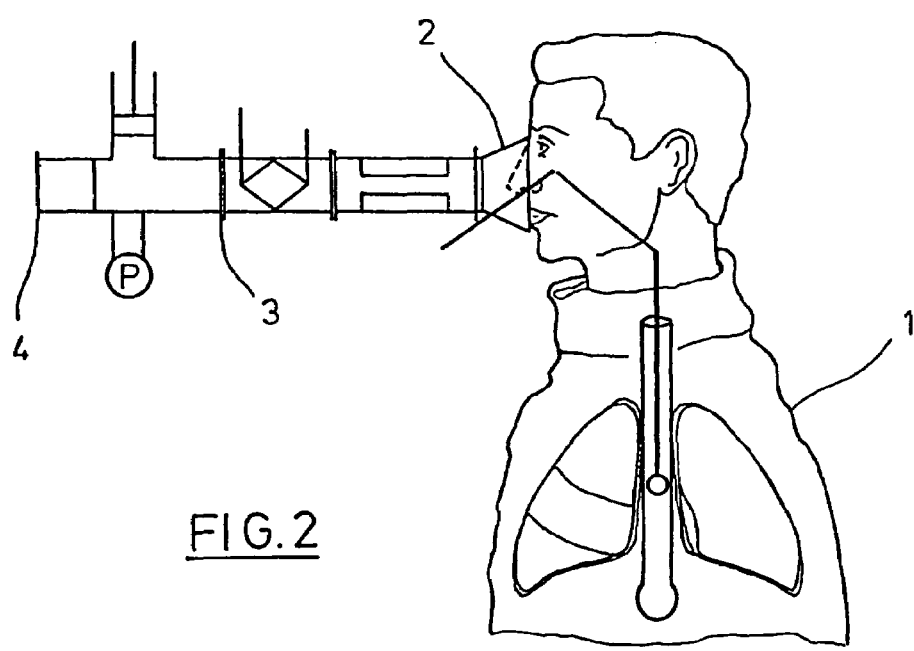
FIG. 2 shows a schematic representation of the principal components in the realization of a CPAP respirator treatment.

FIG. 1 shows in a schematic theoretical representation an apparatus for the control of a respirator device. Here the respirator device is intended for the CPAP respirator treatment of a patient (1). The patient (1) is connected via a breathing mask (2) and a breathing hose (3) to a source of compressed gas (4). The compressed-gas source (4) may be implemented, for instance, as a controllable aerator. In the example of embodiment shown here, one or several sensors (5) are arranged in the area of the breathing mask (2), in order to capture at least one respirator-treatment parameter. However, in accordance with other examples of embodiment the sensors (5) can also be arranged in the area of the breathing hose or in the area of the compressed-gas source (4).

In order to control the compressed-gas source (4) and in order to predetermine respirator-treatment parameter such as, for instance, the respirator-treatment pressure and the respirator-treatment flow, the compressed-gas source (4) is connected to a control (6). In order to support the regulation of a breathing flow, consideration was given in particular to the installation, in the area of the breathing hose (3), of a measuring orifice (7), connected to the control (6) via an evaluation installation (8). Alternatively or in addition to measuring the pressure amplitude of the breathing gas, it is also possible to carry out a phase measurement, with respect to the oscillating components. The respective sensors (5) for pressure measurements and phase measurements may also be connected to the control (6) via evaluation installations (9, 10).

In order to carry out a pattern recognition, at least one of the sensors (5) is connected with an analyzer (11) which is attached to the control (6). The analyzer (11) works together with a storage (12) for the supply of comparative patterns, as well as with a classifier (13) for evaluation support. Particular consideration was given to implementing the control (6), the analyzer (11), the storage (12) as well as the classifier (13) at least in part as the running program of an appropriate data-processing installation. It is also possible to implement the evaluation installation (8, 9, 10) at least in part in the form of software.

The use of a respirator-treatment installation with pattern recognition is possible in particular in the area of CPAP respirator-treatment of a patient (1). With such a respirator-treatment, the timely recognition of a sleep apnea can be promoted by overlaying the volumetric stream produced by the compressed-gas source (4) with a volumetric stream oscillating at low amplitude, produced by a separate pumping installation (P). By evaluating a response signal oscillating at the assigned frequency, one can deduce the respective breathing condition of the patient.

Figure 3:
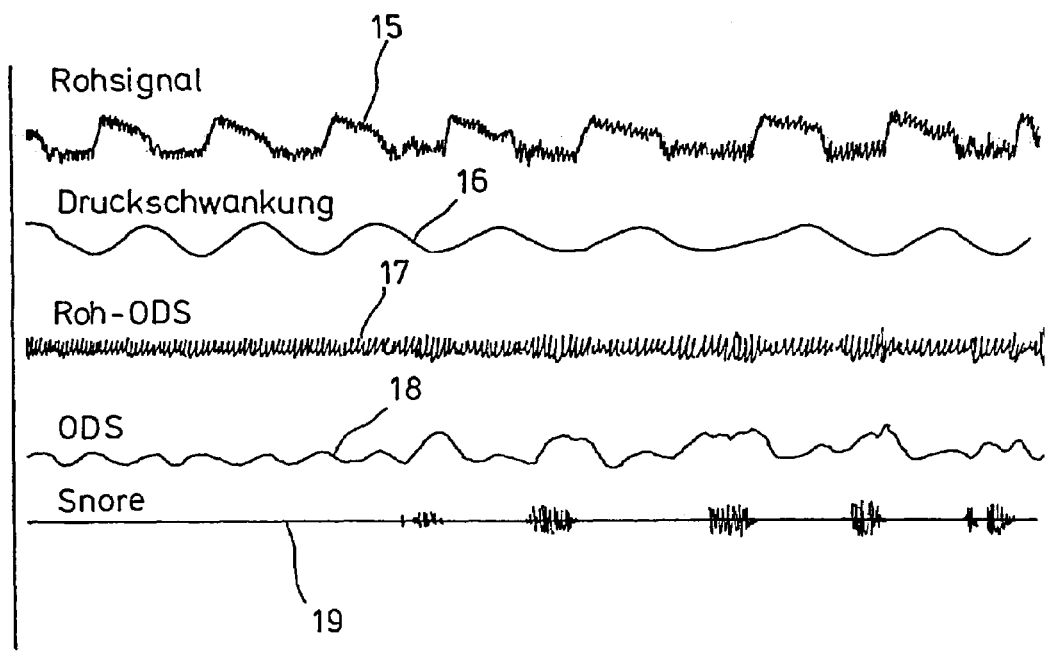
FIG. 3 is a representation of a typical evolution pattern to which pattern recognition is applicable.

FIG. 3 shows typical signal run evolutions when pattern recognition is used. Here the run evolution (15) represents the raw signal; the run evolution (16) corresponds to the pressure variation resulting from the inspiration and expiration processes. By taking into account the run evolution (16) one can produce a run evolution (17) from the run evolution (15) of the raw signal, which [run evolution (17)] corresponds to a raw OPS. After further filtering, one can extract from it a run evolution (18) which corresponds to the OPS. Via a further evaluation one can determine a run evolution (19) which corresponds to a snoring signal.

Figure 4:
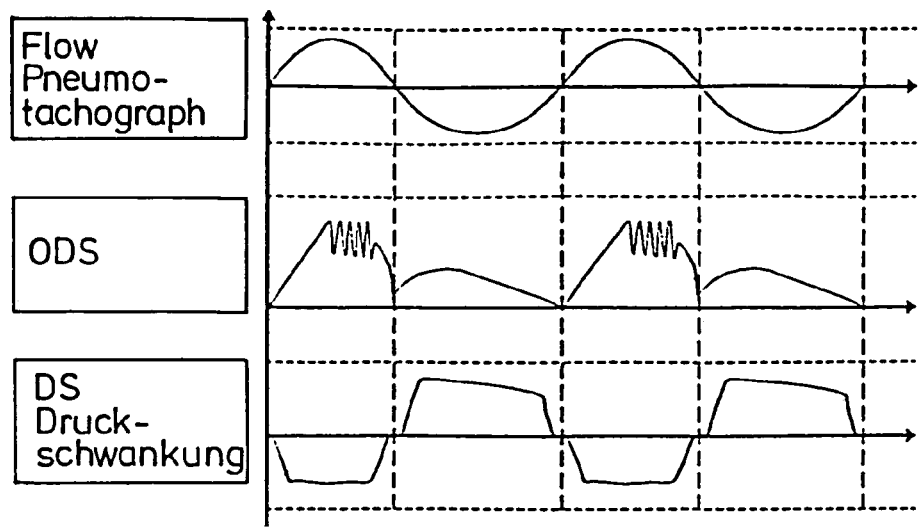
FIG. 4 is a representation of measurement signals in the capture of distinctive form features in the occurrence of snoring.
Figure 5:
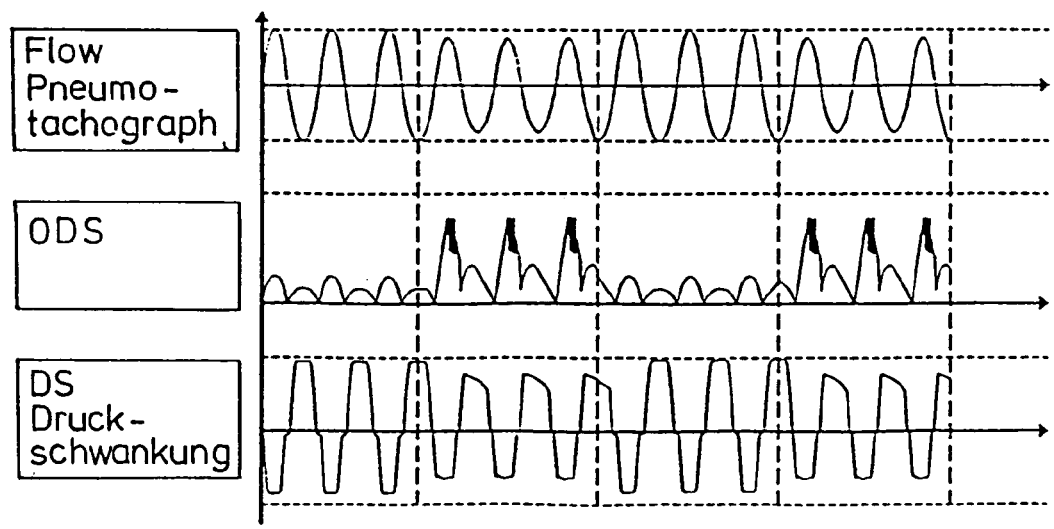
FIG. 5 is a representation similar to the representation in FIG. 4 in a capture of distinctive time features.

The principle of pattern recognition is further explained on the basis of FIG. 4 and FIG. 5, where typical signal evolutions in snoring are explained. FIG. 4 shows a pattern recognition with respect to distinctive form features. They represent the output signal of the FLOW pneumotachygraph; the determined OPS signal; and the pressure variation (PV).

FIG. 5 shows a signal evaluation with respect to distinctive time features. Here again the output signal of the flow pneumotachygraph; the OPS signal; and the PV pressure variation are shown.

As a rule, acute symptoms of sleep apnea only occur for short periods. Typically, during the patient's sleep there occurs the relaxation of tissues in the neck area around the airways, which leads to a closure of the airways. The breathing difficulties that results from the tissue relaxation causes frequent awakening, so that the necessary deep sleep is not achieved. This causes extreme daytime fatigue and deleterious effects on the cardiovascular system.

In order to prevent choking accesses fits, a positive pressure is administered to the sleeping patient in the area of the airways, by means of suitable breathing masks; the positive pressure supports the tissues and counteracts a possible collapse of the tissue with the concomitant constriction of the airways. In order to promote improved breathing comfort it is also possible to supply a higher level of pressure during inspiration and a lower pressure than the former during expiration (because during the expiration process the patient contributes to the total resulting pressure).

In order to supply a respirator-treatment pressure which is suitable for preventing the impairment of the patient's breathing during the occurrence of an acute sleep apnea symptom, but which [pressure] is only built up if it was determined by means of measurements that such a condition could soon occur, it is advantageous that the volumetric stream of breathing gas, provided to the patient in order to support respiration, be overlaid with a volumetric stream oscillating at a defined frequency. Depending on the respective airway geometry of the patient, there corresponds to this oscillating volumetric stream a pressure oscillation whose numerical magnitude is a function of the resistance of the patient's airway.

When this control procedure is implemented, one first determines, in an output state, a base value for the amplitude of the resulting oscillatory pressure run, which [base value] corresponds to an initial normal condition of the patient's airway. In order to account for changes in the base value in the course of the therapy, the base value is thereafter continuously adjusted to current conditions.

The frequency and the volumetric rise of the oscillating volumetric stream are selected in a manner such that the patient is unable to notice any individually capturable effect. Typically the frequency of the oscillatory volumetric stream is in the range of 5 Hz to 20 Hz, generally at 20 Hz; typically the amount of this volumetric stream is only about 1 milliliter of breathing air, which is overlaid oscillatorily on the base volumetric stream of breathing gas.

On the basis of the known frequency of the oscillating signal, one can carry out a selective evaluation of the resulting pressure amplitude, an evaluation which from a measuring technique viewpoint is extremely simple.

In the event that the measurements show a rise in the oscillatory pressure amplitude, the device control raises the actual breathing pressure and thus achieves an enhanced support of the patient's airway tissues. Here, a rise in the pressure amplitude of the oscillating pressure signal indicates that a constriction of the airway is starting to occur. In each case the reference value is the base value for the oscillatory pressure amplitude which had been determined in the normal condition of the patient.

The increase in the respirator-treatment pressure is continued in stepwise fashion with appropriate time delays, until the oscillatory pressure amplitude decreases again and the danger of an acute symptom has passed.

After this condition has been reached the respirator-treatment pressure proper is also decreased again.

Supplementing the pattern recognition it is thus possible to use the evaluation of a test signal to control the respirator device itself, depending on need. In a technical sense, the respirator device itself is no longer provided; instead, what occurs is an as-needed support of the patient's breathing.

To carry out the pattern recognition one can also use, in addition to the previously mentioned signals, say, acoustic signals. Here, an evaluation can refer selectively to low-frequency parts or to high-frequency parts. Such an evaluation is available, for instance, in the analysis of snoring sounds in accordance with FIG. 4 and FIG. 5. By the same token consideration was given to carrying out an evaluation selectively on a narrow-band or broadband basis.

However, the results of the pattern recognition make it possible to draw conclusions not only of the respective respirator-treatment condition of the patient. Over and above that, from specific patterns one can also draw conclusions on the device condition of the respirator, and to recognize functional disturbances in a timely manner. Here, any threat to the patient by a possible device failure can be counteracted by the timely signaling of an impending defect. In this fashion it is also possible to recognize in time any drop in the output capacity of the device.

In general, and depending on the nature of the selected signal, one can obtain different conclusions concerning specific parameters. From the OPS signal one can derive conclusions with respect to the respiratory impedance. For instance, one can use a signal derived from the pressure-variation signal, after filtering out the equal portion, in order to draw conclusions about the CPAP pressure. The respective equal portion provides a conclusion concerning the breathing flow. If the signal is submitted to a band pass in the range from 30 Hz to 300 Hz, conclusions on the snoring signal can be drawn. Upon evaluating electric parameters—say, for instance the motor voltage of the blower—a conclusion concerning the breathing flow may be arrived at. An analysis of the condition of the device may provide, among other pieces of information, data concerning possible leakage conditions in the area of the device itself, or else in the area of hose connections.

Implementing the pattern recognition for the analysis of distinctive form features makes use of a parameter extraction with respect to level and amplitude values; time intervals; envelopes; zero crossings or rises. In the case of an analysis referring to distinctive time features, for instance, one resorts, in a parameter extraction, to periodicities and frequencies.

Above-mentioned explanation concerning the determination of breathing frequency serves as a typical example of the evaluation of the distinctive features of time and amplitude. However, the application of the proposed procedure as well as that of the apparatus are not restricted to this example.

During the implementation of the respirator-treatment therapy, one generally carries out a capture and storage of measured data which individually refer to the patient under therapy. Consequently the information concerning these measured data may be included if a pressure regulation is carried out in subsequent therapies.

Consideration was also given to carrying out a capture and storage of measured data referring to a specific patient population. This brings about the result that the knowledge of these measured data may be utilized in the pressure regulation of individual patients, once it has been ascertained that these individual patients belong to a given patient population.

The recognition of snoring, already explained, may be carried out as explained below.

By means of an analog-digital transformation of the mask pressure with a scanning frequency of 500 Hz followed by a digital band pass filtration in the frequency range of 65 Hz-190 Hz, the pressure variation within the pass range of the filter is interpreted as snoring.

The output values of the filter are assigned to a breathing stage—inspiration and/or expiration. In order to be able to differentiate the output values of flow noises and other artifacts, the conclusion as to a valid true snoring is only adopted after a minimum level has been passed.

Next, the duration of the snoring in relation to the breathing stage—inspiration/expiration is determined. If this quotient exceeds a minimum value, the snoring is considered to deserve therapy, depending on the breathing stage.

The results, before the values are transferred to the pressure control, are as follows:
(a) snoring, yes/no
(b) snoring, at inspiration/expiration
(c) quotient, inspiration time/snoring time.

A recognition of breathing can be carried out as explained below.

By means of an analog-digital transformation of the mask pressure with a scanning frequency of 25 Hz followed by a digital band pass filtration in the frequency range of 0.1 Hz-0.6 Hz, the pressure variation within the pass range of the filter is interpreted as breathing.

The output values of the digital filter assume negative values during inspiration, positive values during expiration. After the inspiration time and expiration time have been determined, one computes the momentary breathing frequency. In order to be able to distinguish the output values from flow noises and other artifacts, one only reaches the conclusion as to a valid true breathing after a minimum level has been passed.

The result before value transfer to the breathing histogram are as follows:
(a) breathing recognized
(b) valid breathing frequency.

A breathing histogram can be determined as described below.

The breathing histogram contains the last 20 breathing frequencies recognized as valid. The breathing frequency recognized as valid by the breathing recognition is transferred to the breathing histogram as a new 20th value. The existing breathing-frequency values are shifted in the breathing histogram by one place, so that there always are 20 breathing frequency values in the breathing histogram.

One determines the most frequently occurring frequency within the breathing histogram. If the frequency with which this frequency occurs exceeds a minimum value, said frequency is valid as the most frequent. This most-often-occurring breathing frequency will be valid as the exclusion criterion for the next following breathing frequency. If the breathing frequency currently recognized as valid deviates from the most-often-occurring breathing frequency by a minimum value, one concludes that it is a breathing artifact.

By determining the most-often-occurring breathing frequency one assumes a stable condition of the breathing, hence of the patient.

The results of the evaluation of the breathing histogram are as follows:
(a) stable breathing condition
(b) breathing artifact, yes/no.

The initialization stage is used to define a base condition of the device. The first minute after turning on the device is used for initialization and communication of the two device parts used. The initialization of the OPS reference-value is concluded after a time span of 2 minutes and after the recognition of a stable breathing frequency by the evaluation of the breathing histogram.

One can implement a pressure control on the basis of OPS rises. If the current OPS value exceeds by at least 60% the OPS reference value established during the initialization, simultaneously with stable condition of breathing, recognized breathing, valid breathing frequency, and recognized inspiration, the pressure value is increased with a rise of 0.2 mbar/sec.

If the current OPS value exceeds the OPS reference value established during the initialization by at least 60% and if simultaneously one of the criteria determined during the breathing analysis does not apply, the pressure is not increased.

For instance, a pressure control on the basis of snoring can be implemented as explained below.

If the current OPS value exceeds the OPS reference value established during the initialization by at least 40%, simultaneously with stable condition of breathing, recognized breathing, valid breathing frequency, recognized inspiration, and exceeding of the minimum value of the quotient inspiration time/snoring time, the pressure value is increased with a rise of 0.1 mbar/sec.

A further variant in the implementation of the procedure as well as in the physical construction of the device consists in producing pressure variations with a frequency which causes a stimulation of the musculature. Such a stimulation of the musculature by means of pressure variation can be called [in English:] Forced Oscillation Technique (FOT). One finds that such pressure variations cause an activation of receptors.

Such receptors are located in the area of the nose, the throat, and the upper airways of a patient. With respect to device control, particular thought was given to carrying out a device control—in a case of recognition of airway closure via the explained possibilities of pattern recognition—in a manner such that pressure oscillations with predetermined frequency and amplitude are generated, leading to an activation of the receptors. Typically, the pressure oscillations are supplied via a nose mark. Preferably the frequencies lie within a range above 0.1 Hz. Particular consideration was given to varying, via the respirator device, both the frequency and the amplitude of the pressure variations, independently of each other. Beyond that it is possible to adaptively vary the duration of the application of the pressure oscillation, as a function of the respectively captured application status, on the basis of an evaluation of the pattern recognitions.

Device-wise one can use, as oscillation generators for the supply of pressure variations, loudspeakers, modified diaphragm pumps, or other agents.

When implementing the signal evaluation, one in particular considers the separation of inspiration signals and expiration signals. This means that the OPS signals for the two stages are separately determined, and that this in particular makes it possible to raise and lower the respirator-treatment pressure solely as a function of the information on inspiration pressure readings. Alternatively it will also be possible to carry out changes in the pressure, both as a function of the inspiration values and as a function of expiration values, yet to affect the pressure differently, depending on whether inspiration or expiration input signals are present.

The invention claimed is:

1. A procedure for the control of a respirator device, in which one can set at least two different pressure levels for a breathable gas supply, comprising:
    capturing at least one respirator-treatment parameter by measurement technique; and
    evaluating the at least one respirator-treatment parameter for the control of a respirator-treament pressure, wherein the at least one respirator-treatment parameter is modified as a function of a pattern recognition, and wherein, in order to carry out the pattern recognition, a time-wise evolution of the at least one respirator-treatment parameter is captured, at least at intervals, and is analyzed with respect to typical evolution patterns;
    based on a pattern recognition, analyzing at least one characteristic of the respirator device selected from the group consisting of defect, reduced performance, leak in the region of the apparatus or in the region of a hose connection; and
    when the analyzing yields a result indicating a functional disturbance or an increased risk of device failure, generating a signal indicative of the functional disturbance or the risk of device failure;
    wherein the two different pressure levels of the respirator device are higher than the air pressure of the environment to support a device function in CPAP therapy.

2. A procedure according to claim 1, wherein an existing pressure level for breathing support is overlaid, at least temporarily, with a stimulating stream oscillating at a defined frequency.

3. A procedure according to claim 1, wherein after a selective evaluation of an oscillatory pressure amplitude, occurring with a frequency of a stimulating stream in the air delivery of a patient, corresponding to a breathing resistance of the patient, a selection of the respective pressure amplitude is carried out.

4. A procedure according to claim 3, wherein at least one electrical signal is evaluated during the pattern recognition.

5. A procedure according to claim 1, wherein a physical signal is evaluated during the pattern recognition.

6. A procedure according to claim 3, wherein a derivation of classes of errors is implemented in a context of the pattern recognition.

7. A procedure according to claim 1, wherein an OPS signal (Oscillating Pressure Signal) is evaluated.

8. A procedure according to claim 1, wherein a static pressure signal is evaluated.

9. A procedure according to claim 1, wherein a pressure variation is evaluated.

10. A procedure according to claim 1, wherein a flow signal is evaluated.

11. A procedure according to claim 1, wherein a signal proportional to at least one of the flow signal and a pressure-dependent signal is evaluated.

12. A procedure according to claim 1, wherein an electrical-drive parameter of a compressed-gas supply is evaluated.

13. A procedure according to claim 1, wherein, in the pattern recognition, distinctive form features are evaluated.

14. A procedure according to claim 1, wherein, in the pattern recognition, distinctive time features are evaluated.

15. A procedure according to claim 1, wherein, following the pattern recognition, a class assignment is carried out.

* * * * *